United States Patent [19]

Bernhard et al.

[11] Patent Number: 5,713,846
[45] Date of Patent: Feb. 3, 1998

[54] IONTOPHORETIC DRUG DELIVERY SYSTEM, INCLUDING METHOD FOR ACTIVATING SAME FOR ATTACHMENT TO PATIENT

[75] Inventors: Michael I. Bernhard, Summit, N.J.; John D. DeNuzzio, Chapel Hill, N.C.

[73] Assignee: Becton Dickinson and Company, Franklin Lakes, N.J.

[21] Appl. No.: 722,814

[22] Filed: Sep. 27, 1996

[51] Int. Cl.⁶ ............................................. A61N 1/30
[52] U.S. Cl. ............................................. 604/20
[58] Field of Search ................................. 604/20, 19

[56] References Cited

FOREIGN PATENT DOCUMENTS

9210235  6/1992  WIPO ........................... 604/20

*Primary Examiner*—Mark Bockelman
*Assistant Examiner*—Ellen Tao
*Attorney, Agent, or Firm*—Allen W. Wark

[57] ABSTRACT

An iontophoretic drug delivery system including a patch, a controller and a magazine. The patch may be secured in a compartment formed in the magazine so that upon insertion of the controller along the magazine to fasten the controller to the patch, a dry drug contained in the patch is hydrated and the patch and controller can be removed from the magazine for attachment to the skin of a patient.

10 Claims, 6 Drawing Sheets

IONTOPHORETIC DRUG DELIVERY SYSTEM, INCLUDING METHOD FOR ACTIVATING SAME FOR ATTACHMENT TO PATIENT

FIELD OF THE INVENTION

The present invention generally relates to iontophoretic drug delivery systems for delivering drugs, medicines, medicaments and the like to patients transdermally, i.e., through the skin, and more specifically relates to an iontophoretic drug delivery system and method for activating same for attachment to the skin of a patient.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastrointestinal tract or punctures in the skin to name a few.

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin. The pair of electrodes is placed in contact with the skin and with the carrier. Current is applied between the two electrodes. Under the influence of the electric field present, the drug molecules migrate through the skin. As current flows between the two electrodes placed at spaced apart locations on the skin, the current path carries the drug with it.

However, with the increasing use of drugs, particularly peptides, peptidomimetics and the like, several disadvantages and limitations have been associated with the activation and use of such devices for delivering such drugs. Specifically, as a result of the need to store the drug in a dry form or otherwise isolate the drug from the aqueous solution in the electrolyte reservoir, such devices have become complicated as disclosed, for example, in U.S. Pat. Nos. 4,722,726 (Sanderson et al.), 4,842,577 (Konno et al.), 4,911,707 (Heiber et al.), 4,917,676 (Heiber et al.), 5,087,242 (Pentelenz et al.), 5,158,537 (Haak et al.), 5,310,404 (Gyory et al.), and 5,385,543 (Haak et al.), the disclosures of which are hereby incorporated by reference in their entirety. In addition, such devices have been generally cumbersome to activate for attachment to the skin of the patient by outpatients and in doctor's offices, and in particular by outpatients having limited mobility or other impairments.

Thus, there has been a need for an iontophoretic drug delivery system which would eliminate the problems and limitations associated with the prior devices discussed above, most significant of the problems being associated with the effort necessary to activate the drug for attachment to the skin of the patient.

SUMMARY OF THE INVENTION

In contrast to the prior devices and systems discussed above, it has been found that a iontophoretic drug delivery system may be constructed in accordance with the present invention which can be easily used to activate the system and apply it to the skin of the patient. Users of such a system may include the patient as well as doctors, nurses and the like, including those having a physical impairment.

The user activated iontophoretic system of the present invention for use in delivering at least one medication through an applied area of a patient, such as the skin, mucus membrane and the like, includes a controller and a patch for attachment to the skin of a patient, the patch including an electrode assembly, the electrode assembly including an electrode reservoir and a drug reservoir containing an active compound to be delivered to the patient, with the drug reservoir being hydratable by manipulating a barrier sealingly separating the reservoirs, and magazine means for securing the patch therein so that upon attachment of the controller to the patch secured in the magazine, the barrier is manipulated to bring the reservoirs into fluid communicating contact with one another so that the drug is dissolved in an aqueous solution contained in the electrode reservoir.

In the preferred embodiment of the iontophoretic drug delivery system, the means includes a bottom member and two foldable side members extending along at least two sides of the bottom member. Also, the bottom member includes a compartment for accommodating the patch therein and a notch for securing at least a portion of the barrier therein. In addition, the foldable side members form a guide and a slot for accommodating the controller, whereby the controller may be inserted into the guide and slide along the slot and fastened to the patch. Further, the iontophoretic drug delivery system includes a supporting structure to which the patch is releasably attached.

The method of the present invention for activating an iontophoretic drug delivery device for iontophoretically delivering at least one medication through an applied area of a patient such as the skin, mucus membrane or the like, includes the steps of placing a patch for attachment to the skin of a patient into a compartment formed in a magazine, the magazine including a bottom member and two foldable extending side members, and the patch including an electrode reservoir and a drug reservoir containing an active compound to be delivered to the patient, with the drug reservoir being hydratable by manipulating a barrier sealingly separating the reservoirs, folding the side members towards one another to secure the patch in the compartment, inserting a controller into a guide formed by the side members along a slot into contact with the patch to fasten the controller to the patch, removing the patch with the controller fastened thereto from the magazine, and manipulating the barrier and bringing the reservoirs into fluid communicating contact with one another so that the drug is dissolved in an aqueous solution contained in the electrode reservoir.

In the preferred embodiment of the method, the step of manipulating the barrier includes pulling a tab. Also, the method includes the step of removing the patch and the controller from a supporting structure for application to the skin of the patient. In addition, the step of bring the reservoirs into contact with one another includes hydrating the drug reservoir or dissolving the drug contained in the drug reservoir into the electrode reservoir.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

DETAILED DESCRIPTION OF THE PREFERRED EMBODIMENT

The iontophoretic drug delivery system of the present invention is illustrated in FIGS. 1–4 and generally includes the designation 10. Referring to FIGS. 1–4, the device or system 10 of the present invention includes a patch 12, a controller 14 and a magazine 16.

Figure 1:
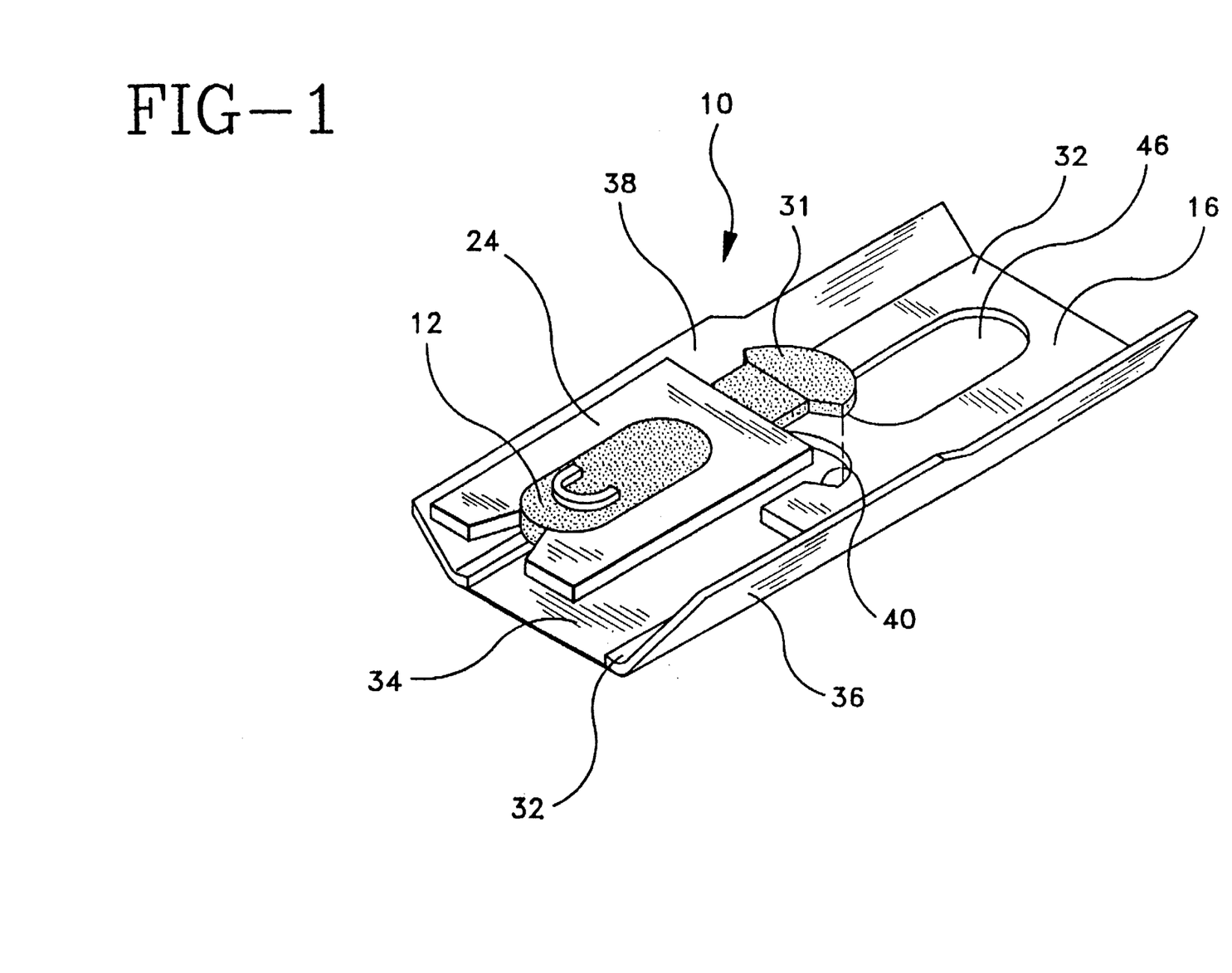
FIG. 1 is a perspective view of the iontophoretic drug delivery system of the present invention showing the patch for insertion into a magazine, with FIG. 1A being an enlarged, cross-sectional side view of the patch.
Figure 1A:
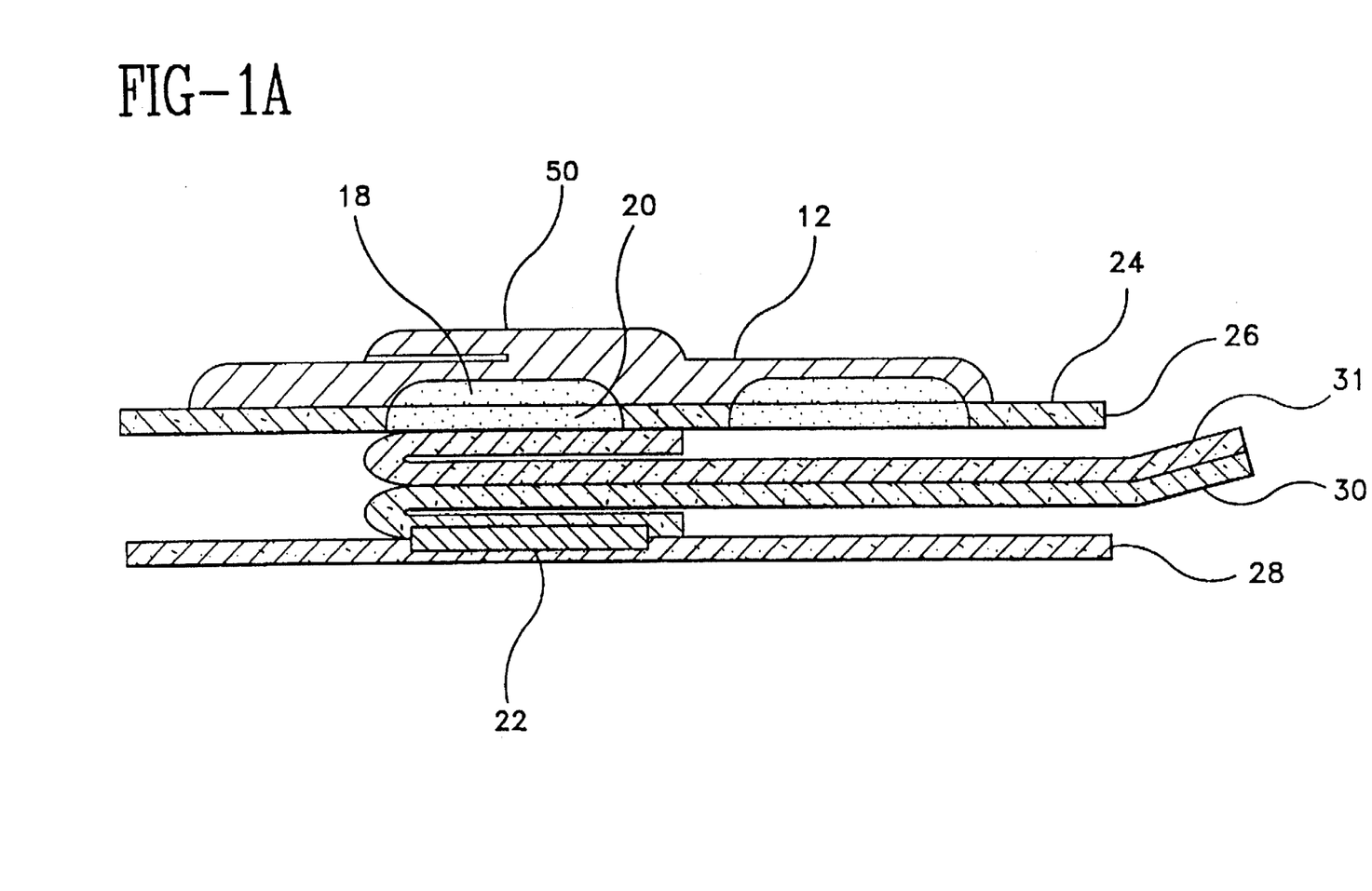

As illustrated in FIG. 1, and in greater detail in FIG. 1A, the patch 12 includes an electrode assembling, having at least one electrode, an electrode reservoir 20 and at least one drug reservoir 22, which are preferably held together by a suitable supporting structure 24 divided or otherwise separated into two portions, with one portion 26 (upper) including the electrode assembly 18 and the electrode reservoir 20 and the other portion 28 (lower) including the drug reservoir 22 which holds the medication or drug, preferably in an ionized or ionizable form, to be delivered iontophoretically as disclosed in co-pending application Ser. No. 08/722,813 entitled "USER ACTIVATED IONTOPHORETIC DEVICE AND METHOD FOR ACTIVATING SAME," the disclosure of which is hereby incorporated by reference in its entirety. The two portions of the supporting structure 24 are sealed separately by a barrier 30 extending from the structure 24, which can be manipulated to bring the drug reservoir and the electrode reservoir into fluid conducting contact with one another. In this way, the drug contained in the drug reservoir can be stored or otherwise sealingly isolated from the electrode reservoir in the first portion, in a dry state or formulation in a matrix or on a supporting substrate for hydration prior to use.

Figure 2:
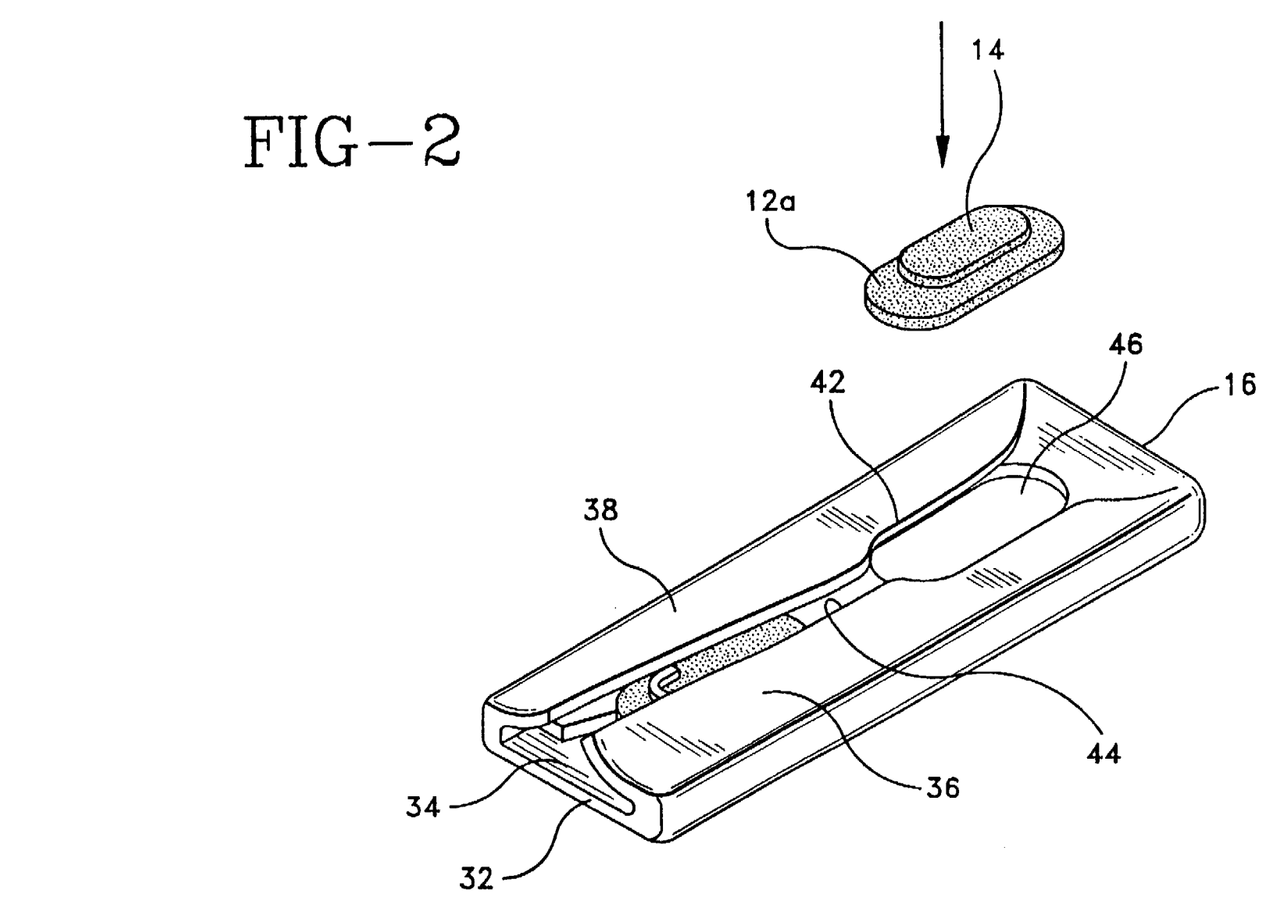
FIG. 2 is a perspective view of the iontophoretic drug delivery system illustrated in FIG. 1 with the patch inserted therein and the magazine closed for use and insertion of the controller therein.

Referring to FIG. 1, the magazine 16 includes bottom planar member 32 having a compartment 34 for accommodating the patch 12. Extending along the sides of the bottom member are two extending side members 36, 38, which are closeable about the compartment (FIG. 2). The compartment 34 also includes a notch 40 in which the extending portion or tab 31 of the barrier 30 may be nestled (FIG. 1). In addition, each side 36, 38 of the magazine 16 includes a tapered portion, which together form a guide 42 to a slot 44 running above the compartment 34.

Figure 3:
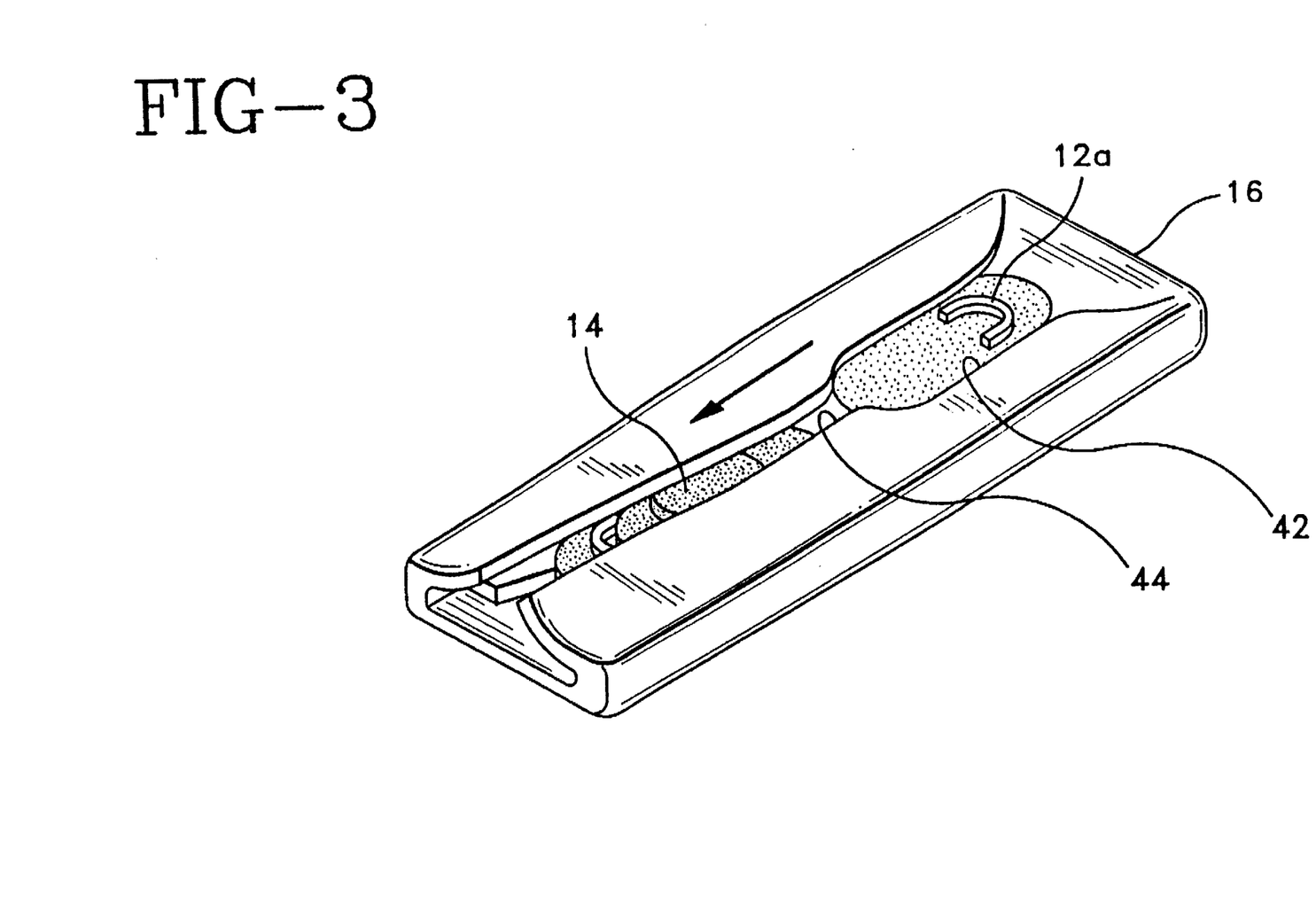
FIG. 3 is a perspective view of the iontophoretic drug delivery system illustrated in FIG. 2 with the controller being attached to the patch.

As illustrated in FIGS. 2 and 3, the controller 14 is preferably reusable and releasably attached to the patch 12 by sliding, attaching or snapping the controller into the fastener 50 extending from the top of the patch (FIG. 1A). The particular controller is not essential to the present invention, and may include, for example, those disclosed in co-pending patent application Ser. Nos. 08/315,532, entitled "IONTOPHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER," 08/315,533 entitled "IONTOPHORESIS ASSEMBLY INCLUDING CLEANABLE ELECTRICAL CONTACTS," 08/315,372, now U.S. Pat. No. 5,645,526 entitled "APPARATUS AND METHOD FOR ENSURING COMPATIBILITY OF A REUSABLE IONTOPHORETIC CONTROLLER WITH AN IONTOPHORETIC PATCH," and 08/534,897, now abandoned entitled "IONTOPHORETIC DRUG DELIVERY SYSTEM, INCLUDING REUSABLE DEVICE," and U.S. Pat. No. 5,498,235 (Flower), the disclosures of which are hereby incorporated by reference in their entirety. It should be appreciated that the particular means for releasably attaching the controller 14 to the patch 12 is not essential to the present invention and is simply a matter of choice.

In the preferred embodiment illustrated in FIGS. 2 and 3, the bottom member of the magazine includes a compartment 46 for accommodating a used patch 12A with the controller 14 fastened thereto. In this way, the controller (reusable) with the used patch fastened thereto, can be placed in the compartment (FIG. 2). Then, the controller can be slid to remove it from the used patch 12A. It should also be appreciated that at the guide 42 formed by the extending side members can be dimensioned so as to at least partially cover the compartment 46. In this way, the controller and the used patch 12A can be placed into the compartment 46. Also, the patch 12 can be placed into the magazine 16 and pre-assembled before the side members are folded and thereafter folded to secure the used patch 12A in the magazine.

Operation and Use

Having described one embodiment of the iontophoretic drug delivery system 10, including the disposable patch 12, controller 14, and magazine 16 of the present invention, its operation and use is described below in connection with FIGS. 1–4.

Figure 4:
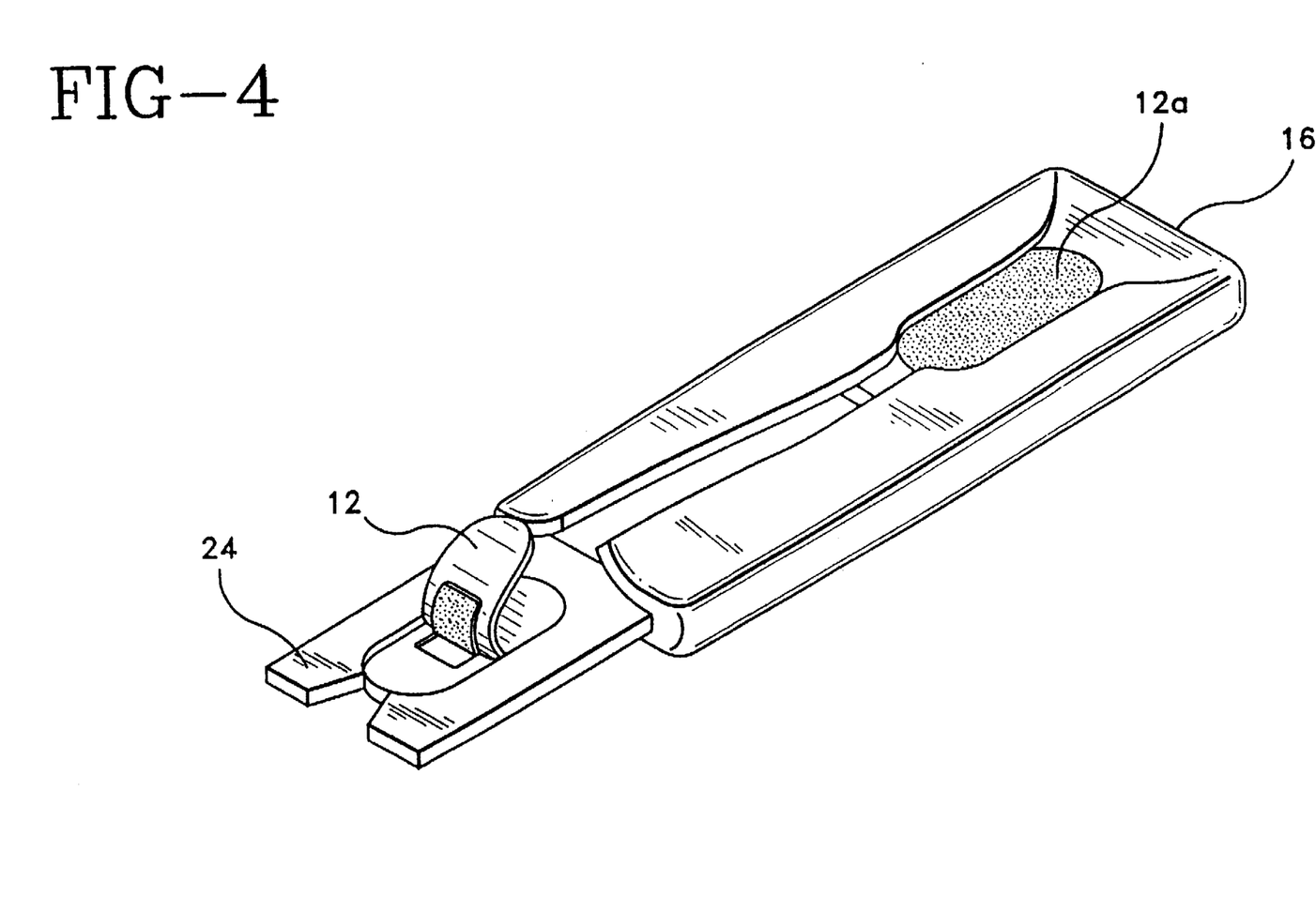
FIG. 4 is a perspective view of the iontophoretic drug delivery system illustrated in FIG. 3 showing the patch with the controller fastened thereto being removed from the magazine, with FIG. 4A being an enlarged, cross-sectional side view of the patch and controller being removed from the supporting structure for attachment to the skin of a patient.
Figure 4A:
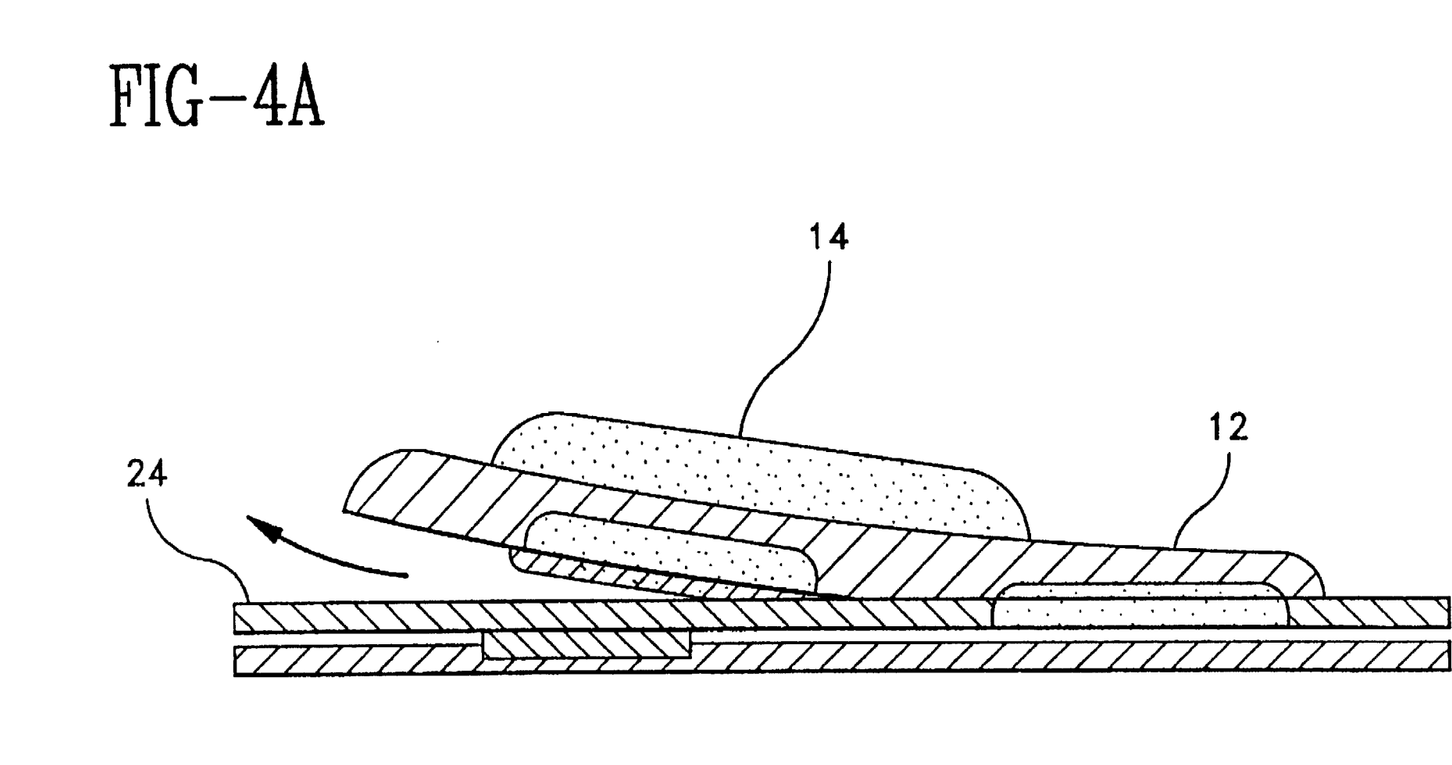

As illustrated in FIG. 1, the patch 12 and supporting structure 24 are placed into the compartment 34, with the extending tab 31 of the barrier 30 secured in the notch 40 prior to use. The side members 36, 38 are folded to secure the patch 12 and supporting structure in the magazine 16 and to form the guide 42 and slot 44 (FIG. 2). Next, to use the system 10, the controller 14 along with a used patch 12A is inserted into the guide 42 and compartment 46 and the controller 14 is removed from the used patch and moved along the slot into contact with the faster 50 on the top of the new patch 12 (FIG. 3). Then, the user continues to slide the controller 14, with the patch 12 fastened thereto, along the slot to force the controller 12 and patch 12, along with the supporting structure, from the magazine 16 so that the patch 12 and controller 14 can be peeled or otherwise removed from the supporting structure 24 (FIGS. 4 and 4A).

Because the tab 31 is secured in the notch 40, the sliding action forces the barrier 30 to be pulled from the supporting structure 24 to expose the reservoirs. Specifically, the pulling action causes the barrier 30 to be drawn forward exposing electrode reservoir and the drug reservoir containing drug (active compound) to be delivered to the patient. In this way, upon manipulation, the electrode reservoir and the drug reservoir are brought into fluid conducting contact with one another and the drug may be dissolved at the interface of the reservoirs, due to its solubility in an aqueous fluid and/or the drug reservoir is hydrated and adhered to the interface of the electrode reservoir. Thereafter, the patch 12, with the controller 14 fastened thereto and the barrier removed, can be attached to the skin of the patient to deliver the drug.

As is well known within the field, the device can be attached to a suitable area of the skin of the patient, with the drug containing patch in electrical conducting contact with the skin, and a voltage impressed across the electrodes of the electrode assembly to cause current to flow through the skin of the patient to drive the drug into the skin and the tissue to be absorbed by the body of the patient for the desired period of time. It should also be appreciated that the device of the present invention can be applied to other areas of the body such as mucus membranes depending upon the desired therapy and drugs to be delivered.

Also, it should be appreciated that although the method of the present invention has be described in connection with the magazine wherein the patch 12 and controller 14 are placed into the magazine, the patch 12, controller 14, and the magazine may be pre-assembled for use by the users, which would simply involve sliding the controller to fasten it to the patch so that the controller and patch, with the supporting structure can be removed from the magazine.

In this way, the magazine can be used to collect and properly dispose of used patches 12A, or merely as an aid to attaching the controller to the new patch.

Active agent, drug, formulation, medication, medicament and active compound have been used herein to mean any pharmaceutical agent, such as therapeutic compounds, diagnostic agents, anesthetic agents and the like.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

While the preferred embodiments of the present invention has been described so as to enable one skilled in the art to practice the system and method of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A user activated iontophoretic system for use in delivering at least one medication through an applied area of a patient, such as the skin, mucus membrane and the like, comprising:

a controller and a patch for attachment to the skin of a patient, the patch including an electrode assembly, said electrode assembly including an electrode reservoir and a drug reservoir containing an active compound to be delivered to the patient, with said drug reservoir being hydratable by manipulating a barrier sealingly separating said reservoirs; and magazine means for securing said patch therein so that upon attachment of said controller to said patch secured in said magazine, said magazine means including means for manipulating said barrier to bring the reservoirs into fluid communicating contact with one another so that said drug is dissolved in an aqueous solution contained in said electrode reservoir.

2. An iontophoretic drug delivery system as defined in claim 1, further comprising a supporting structure to which said patch is releasably attached.

3. An iontophoretic drug delivery system as defined in claim 1, wherein the means includes a bottom member and two foldable side members extending along at least two sides of said bottom member.

4. An iontophoretic drug delivery system as defined in claim 3, wherein said bottom member includes a compartment for accommodating said patch therein and a notch for securing at least a portion of said barrier therein.

5. An iontophoretic drug delivery system as defined in claim 3, wherein said foldable side members form a guide and a slot for accommodating said controller, whereby said controller may be inserted into said guide and slide along said slot and fastened to said patch.

6. A method of activating an iontophoretic drug delivery device for iontophoretically delivering at least one medication through an applied area of a patient such as the skin, mucus membrane or the like, comprising the steps of:

placing a patch for attachment to the skin of a patient into a compartment formed in a magazine, said magazine including a bottom member and two foldable, extending side members, and said patch including an electrode reservoir and a drug reservoir containing an active compound to be delivered to the patient, with said drug reservoir being hydratable by manipulating a barrier sealingly separating said reservoirs;

folding said side members towards one another to secure said patch in said compartment;

inserting a controller into a guide formed by said side members along a slot into contact with said patch to fasten said controller to said patch;

removing said patch with said controller fastened thereto from said magazine; and manipulating said barrier and bringing the reservoirs into fluid communicating contact with one another so that said drug is dissolved in an aqueous solution contained in said electrode reservoir.

7. A method as defined in claim 6, wherein the step of manipulating said barrier includes pulling a tab.

8. A method as defined in claim 6, further comprising the step of removing the patch and said controller from a supporting structure for application to the skin of the patient.

9. A method as defined in claim 6, wherein said step of bringing said reservoirs into contact with one another includes hydrating said drug reservoir.

10. A method as defined in claim 6, wherein said step of bringing said reservoirs into contact with one another includes dissolving the drug contained in said drug reservoir into said electrode reservoir.

* * * * *